(12) United States Patent
St. Germain et al.

(10) Patent No.: US 6,848,448 B1
(45) Date of Patent: Feb. 1, 2005

(54) DEVICES AND METHODS FOR CEREBRAL PERFUSION AUGMENTATION

(75) Inventors: Jon P. St. Germain, Maple Grove, MN (US); Peter T. Keith, Maple Grove, MN (US); Denise R. Barbut, New York, NY (US); Steven W. Berhow, Maple Grove, MN (US); Joel R. Munsinger, Maple Grove, MN (US)

(73) Assignee: CoAxia, Inc., Maple Grove, MN (US)

( * ) Notice: Subject to any disclaimer, the term of this patent is extended or adjusted under 35 U.S.C. 154(b) by 366 days.

(21) Appl. No.: 10/057,252

(22) Filed: Jan. 23, 2002

(51) Int. Cl.[7] ............................................... A61B 19/00
(52) U.S. Cl. ...................................... 128/898; 606/194
(58) Field of Search ................. 128/898; 601/151–152; 604/96.01; 606/191–192, 194, 198, 202, 203

(56) References Cited

U.S. PATENT DOCUMENTS

| | | | |
|---|---|---|---|
| 5,195,942 A | 3/1993 | Weil et al. | |
| 5,531,776 A | 7/1996 | Ward et al. | |
| 5,716,386 A | 2/1998 | Ward et al. | |
| 6,161,547 A | 12/2000 | Barbut | |
| 6,190,304 B1 | 2/2001 | Downey et al. | |
| 6,231,551 B1 | 5/2001 | Barbut | |
| 6,296,654 B1 | 10/2001 | Ward | |

*Primary Examiner*—Thomas Barrett
(74) *Attorney, Agent, or Firm*—O'Melveny & Myers LLP

(57) ABSTRACT

Methods are provided for cerebral perfusion augmentation in patients suffering from global or focal cerebral ischemia. Methods include partial or complete obstruction of the femoral or iliac arteries or the inferior vena cava, external compression of the iliac, femoral, or brachial arteries, placing the patient in a trendelenberg position, applying one or more compression members to the extremities, or removing portion(s) of cerebral spinal fluid. Partial obstruction of a vessel can be accomplished by a device comprising an elongate catheter and a distally mounted expandable member. The expandable member may comprise one or two balloons. Other medical devices, such as an angioplasty, stent, or atherectomy catheter, can be inserted distal the expandable member to provide additional therapeutic intervention.

8 Claims, 8 Drawing Sheets

DEVICES AND METHODS FOR CEREBRAL PERFUSION AUGMENTATION

FIELD OF THE INVENTION

The present invention relates generally to methods and devices for augmenting blood flow to a patient's vasculature. More particularly, the invention relates to apparatus and methods that augment cerebral perfusion in patients with global or focal ischemia. The devices and methods include partial obstruction ("coarctation") to the peripheral blood vessels to alter blood flow patterns in various portions of the human vasculature.

BACKGROUND OF THE INVENTION

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. Shock is the state in which failure of the circulatory system to maintain adequate cellular perfusion results in reduction of oxygen and nutrients to tissues. Within minutes of circulatory failure, tissues become ischemic, particularly in the heart and brain.

The two common forms of shock are cardiogenic shock, which results from severe depression of cardiac performance, and hemorrhagic shock, which results from trauma. The most frequent cause of cardiogenic shock is myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, acutely acquired ventricular septal defects, can also cause cardiogenic shock by reducing cardiac output. Additional causes of cardiogenic shock include cardiac arrhythmia, such as ventricular fibrillation. Hemorrhagic shock is typically the result of penetrating injuries caused by, for example, traffic accidents and gunshot wounds. In this case, cardiac function is unimpaired and the cause of shock is circulatory blood loss.

Treatment of global cerebral ischemia involves treating the source of the systemic circulatory failure and ensuring adequate perfusion to the central nervous system. For example, treatment of cardiogenic shock due to prolonged cardiopulmonary bypass consists of cardiovascular support with the combination of inotropic agents such as dopamine, dobutamine, and intra-aortic balloon counterpulsation. Treatment of hemorrhagic shock consists of volume replacement and hemostasis. When these measures fail, supracoeliac aortic clamping is used. Vasoconstrictors, such as norepinephrine, are also administered systemically to maintain systolic blood pressure (ideally above 80 mmHg). Unfortunately, these agents produce pressure at the expense of flow, particularly blood flow to small vessels such as the renal arteries. The use of the vasoconstrictors is, therefore, associated with significant side effects, such as acute renal failure, congestive heart failure, and cardiac arrhythmias.

Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system and is the result of a disturbance of the cerebral circulation. Other causes of focal cerebral ischemia include vasospasm due to subarachnoid hemorrhage or iatrogenic intervention.

Traditionally, emergent management of acute ischemic stroke consists of mainly general supportive care, e.g. hydration, monitoring neurological status, blood pressure control, and/or anti-platelet or anti-coagulation therapy. Heparin has been administered to stroke patients with limited and inconsistent effectiveness. In some circumstances, the ischemia resolves itself over a period of time because some thrombi get absorbed into the circulation, or fragment and travel distally over a period of a few days. In June 1996, the Food and Drug Administration approved the use of tissue plasminogen activator (t-PA) or Activase®, for treating acute stroke. However, treatment with systemic t-PA is associated with increased risk of intracerebral hemorrhage and other hemorrhagic complications. Vasospasm may be partially responsive to vasodilating agents. The newly developing field of neurovascular surgery, which involves placing minimally invasive devices within the carotid arteries to physically remove the offending lesion, may provide a therapeutic option for these patients in the future, although this kind of manipulation may lead to vasospasm itself. Iatrogenic vasospasm and vasospasm caused by subarachnoid hemorrhage may respond to treatment with aortic constriction.

In both global and focal ischemia, patients develop neurologic deficits due to the reduction in cerebral blood flow. One treatment may include the use of devices to increase blood flow to the cerebral vasculature as the sole therapy. Alternatively, treatments include measures to increase blood flow to the cerebral vasculature to maintain viability of neural tissue, thereby increasing the length of time available for any adjunct interventional treatment and minimizing neurologic deficit while waiting for resolution of the ischemia. Augmenting blood flow to the cerebral vasculature is not only useful in treating occlusive or vasospastic cerebral ischemia, but may also be useful during interventional procedures, such as carotid angioplasty, stenting or endarterectomy, which might otherwise result in focal cerebral ischemia, and also cardiac procedures which may result in cerebral ischemia, such as cardiac catheterization, electrophysiologic studies, and angioplasty.

New devices and methods are thus needed for augmentation of cerebral blood flow in treating patients with either global or focal ischemia caused by reduced perfusion, thereby minimizing neurologic deficits.

SUMMARY OF THE INVENTION

The devices and methods described herein will find use in treating patients with acute ischemic stroke, cardiogenic shock, and other conditions of reduced cerebral perfusion. In one embodiment, the invention provides devices for partial or complete vascular obstruction, and methods for augmenting blood flow to a patient's cerebral vasculature, including the carotid and vertebral arteries. The term obstruction refers to partial or complete blockage of a vessel, and to any of the devices that provide such blockage. The devices include an expandable member distally mounted on a catheter for delivery to a vessel, such as the aorta, iliac arteries, femoral arteries, brachial arteries, and inferior vena cava. The expandable member is collapsed to facilitate insertion into and removal from the vessel, and expanded during use to at least partially obstruct blood flow.

In one embodiment, the devices comprise an elongate catheter having a proximal and a distal region. The catheter may also have a lumen extending between the proximal and distal regions. An expandable member, e.g., a balloon in certain cases, is carried at the distal region of the catheter. The catheter in certain embodiments may include a second expandable member carried at the distal region of the catheter, proximal the first expandable member. In certain embodiments, the catheter will also include blood pressure measuring capabilities distal and/or proximal the first and/or second (when present) expandable members.

In use, a baseline cerebral flow or carotid flow is measured. The catheter having one expandable member is located in the right or the left femoral artery through an incision in the femoral region. Alternatively, the catheter is inserted in both the right and the left femoral arteries. The expandable device(s) are then expanded to partially or completely obstruct the femoral arteries. Cerebral blood flow and/or cerebral blood pressure rises and is maintained at an increased level as desired. Cephalad blood pressure and/or cerebral blood flow may be monitored, and the expandable device adjusted as needed to achieve a desired increase in cerebral blood flow. The desired increase in cerebral blood flow may be approximately 20% or more, 25% or more, 30% or more, 40% or more, 50% or more, 60% or more, 70% or more, 80% or more, 90% or more, or 100% or more of the measured baseline cerebral blood flow. Therapeutic instruments may be deployed through the lumen (when present) of the catheter to perform procedures cephalad. Devices, such as infusion, atherectomy, angioplasty, hypothermia catheters or devices (selective cerebral hypothermia with or without systemic hypothermia), or electrophysiologic study (EPS) catheters, can be introduced through the constrictor to insert in the vessel to provide therapeutic interventions at any site rostrally. Typically hypothermia will be combined with measures to increase perfusion to overcome the decreased cerebral blood flow caused by the hypothermia, such that hypothermia and vascular restriction, i.e., coarctation, are complimentary. Where cerebral cooling is desired in combination with coarctation, a cooling catheter can be introduced through the constrictor to insert into a desired vessel. Alternatively, cooling catheter devices can be inserted through the constrictor to infuse cool blood selectively into one side of the brain. Devices and methods described in U.S. application Ser. No. 09/792,732, filed Feb. 23, 2001, Ser. No. 09/792,600, filed Feb. 23, 2001, Ser. No. 09/483,370, filed Jan. 14, 2000, Ser. No. 09/256,965, filed Feb. 24, 1999, 60/076,222, filed Feb. 25, 1998, 60/096,218, filed Aug. 12, 1998, and U.S. Pat. Nos. 6,161,547, 6,165,199, and 6,146,370, all incorporated herein by reference in their entirety, can be used for cooling or other procedures.

In another method, the expandable devices described above are inserted into the right and/or the left common iliac arteries or external iliac arteries. The expandable device(s) are then expanded to partially or completely obstruct each iliac artery. Alternatively, occlusion of both the iliac arteries may be achieved by inserting a single catheter having two expandable members, such as balloons. Cerebral blood flow and/or cerebral blood pressure rises and is maintained at an increased level as desired. The level of occlusion of the right and/or left iliac arteries may be adjusted to achieve a desired increase in cerebral blood flow. In this manner, blood in the peripheral arteries is diverted to the cerebral vasculature, thereby increasing cerebral perfusion and minimizing neurological deficit. By selectively increasing cerebral blood flow, the use of systemically administered vasoconstrictors or inotropic agents to treat shock may be reduced or eliminated.

In still another method, the right and/or the left femoral arteries or iliac arteries are compressed externally to achieve a desired increase in cerebral flow. The external compression may be achieved by applying a "c-clamp" or tourniquet to the arteries after incision(s) are made over the arteries. Alternatively, external manual compression can be used without making any incision.

In still another method, an expandable device as described above is inserted into the inferior vena cava to partially or completely obstruct venous return from the extremities. The increase in venous pressure is transmitted through the capillary bed to the arterial circulation of the lower extremities and ultimately to the aorta, thereby enhancing cerebral blood flow.

In still another method, the patient is placed in a trendelenberg position at an angle from horizontal after a baseline cerebral blood flow is measured. With the patient's head lower than the level of the heart, cerebral blood flow increases. The angle of the patient in the trendelenberg position is adjusted to achieve a desired increase in cerebral blood flow.

In still another method, compression pants (for one or both legs) or compression cuffs (for one or both arms) are applied to the patient's extremities to compress the peripheral vessels, thereby causing augmentation of cerebral blood flow. The degree of compression is adjusted to achieve a desired increase in cerebral blood flow.

In still another method, a portion of cerebral spinal fluid is removed from the patient either by a lumbar puncture, cerebellomedullary cistern puncture, or through a burr hole. Removal of cerebral spinal fluid allows more space within the brain for cerebral blood flow. A second, third, or more portion of cerebral spinal fluid may be removed to achieve a desired increase in cerebral blood flow. This method (and other cerebral blood flow enhancing devices and methods described herein) can be used in combination with any of the other cerebral blood flow enhancing devices and methods described herein.

It will be understood that there are many advantages in using the cerebral blood flow enhancing devices and methods disclosed herein. For example, the devices can be used (1) to provide variable partial obstruction of a vessel; (2) to augment and maintain cerebral perfusion in patients suffering from global or focal ischemia; (3) to prolong the therapeutic window in global or focal ischemia; (4) to accommodate other medical devices, such as an atherectomy catheter; (5) prophylactically by an interventional radiologist, neuroradiologist, or cardiologist in an angiogram or fluoroscopy suite; (6) for prevention of cerebral ischemia in patients undergoing procedures, such as coronary catheterization or surgery, where cardiac output might fall as a result of arrhythmia, myocardial infarction or failure; (7) to treat certain forms of shock, thereby eliminating or reducing the use of systemic vasoconstrictors; (8) to prevent hypotensive neurologic damage during carotid stenting, and (9) to reverse vasospasm induced by hemorrhage or interventional procedures.

DETAILED DESCRIPTION

The devices and methods disclosed herein are to be used in treating patients suffering from global cerebral ischemia due to systemic circulatory failure, and focal cerebral ischemia due to thromboembolic occlusion or vasospasm of the cerebral vasculature. However, it will be understood that the devices and methods can be used in other medical conditions.

Figure 1:
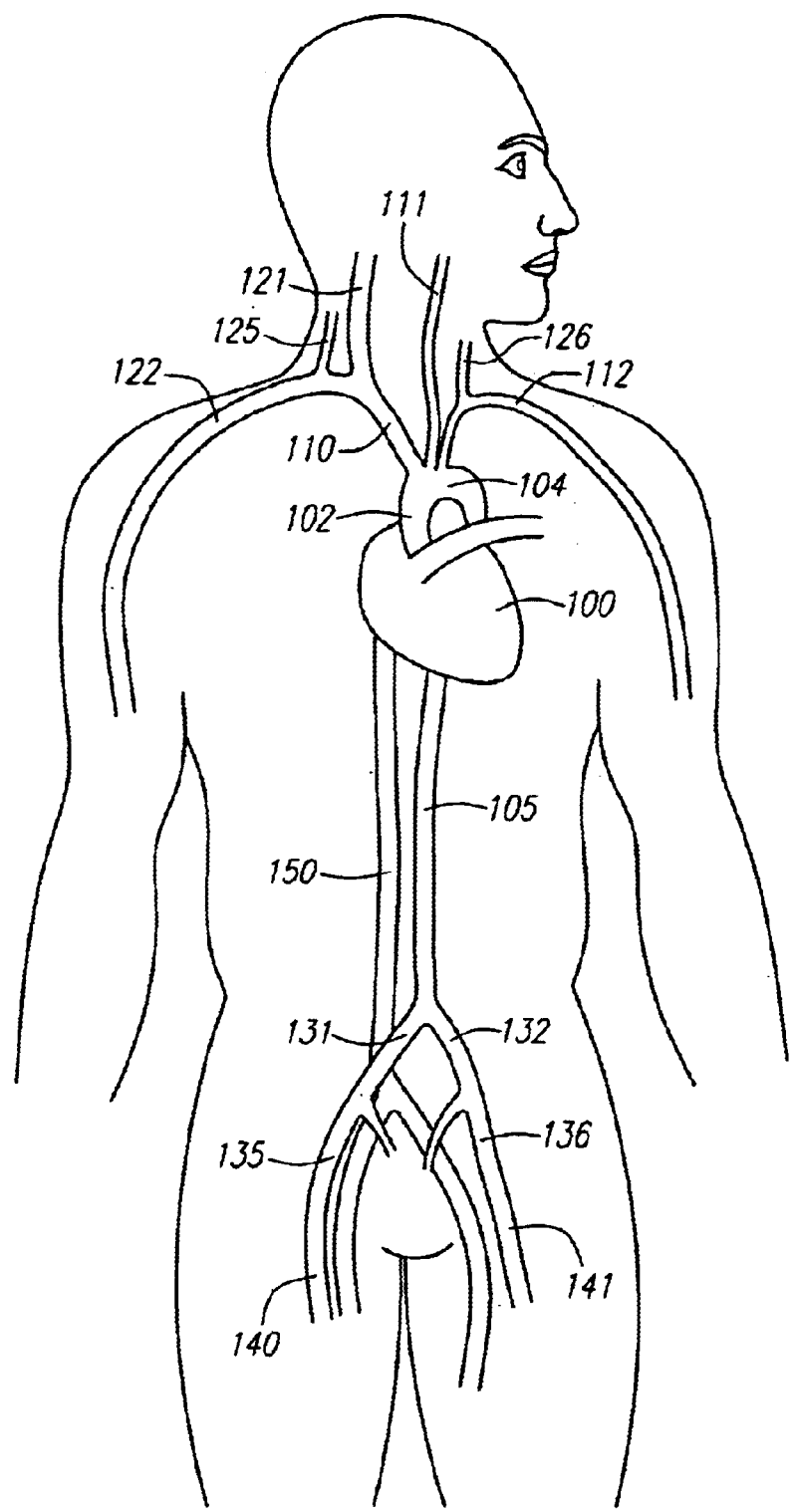
FIG. 1 depicts a patient's systemic circulation relevant to the present invention.

Systemic circulation relevant to the methods of the present invention is shown in FIG. 1. During systole, oxygenated blood leaving heart 100 enters the aorta, which includes ascending aorta 102, aortic arch 104, and descending aorta 105. The aortic arch gives rise to brachiocephalic trunk 110, left common carotid artery 111, and left subclavian artery 112. The brachiocephalic trunk branches into right common carotid artery 121 and right subclavian artery 122. The right and left subclavian arteries, respectively, give rise to right vertebral artery 125 and left vertebral artery 126. Further distally, right and left subclavian arteries give rise to right and left brachial arteries within each respective arm. Descending aorta 105 branches into right common iliac artery 131 and left common iliac artery 132. The right common iliac artery gives rise to right external iliac artery 135 which continues to become right femoral artery 140. The left common iliac artery gives rise to left external iliac artery 136 which continues to become left femoral artery 141. Blood in the right and left femoral arteries perfuses the lower extremities and returns to the heart through inferior vena cava 150.

Figure 2A:
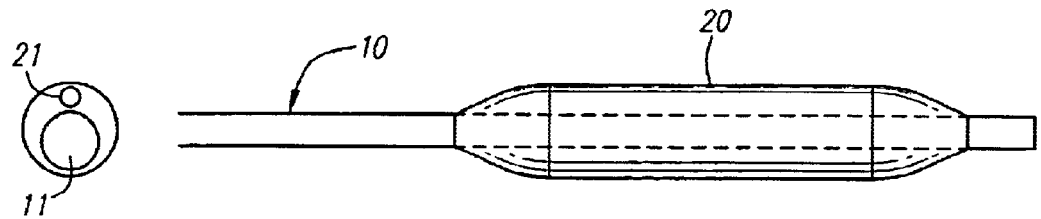
FIG. 2A depicts an embodiment of the devices constructed according to the present invention for providing partial obstruction of a vessel.
Figure 2B:
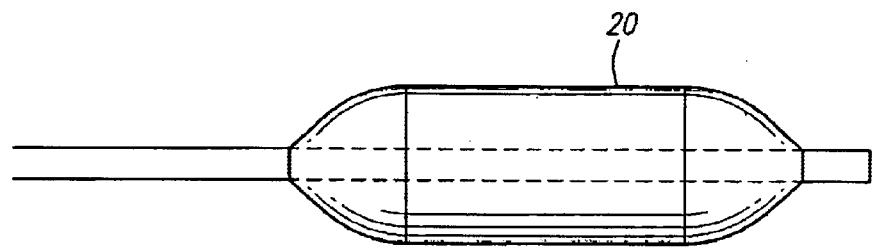
FIG. 2B depicts the inflation of an expandable member of the device of FIG. 2A.

In one embodiment as shown in FIG. 2A, the obstruction device comprises elongate catheter 10 having lumen 11 that communicates with a proximal end and a distal end. The distal end has an expandable member, e.g., a balloon. Balloon 20 communicates with inflation lumen 21. FIG. 2B depicts expansion of balloon 20. In certain embodiments, the distal end of the catheter includes a radiopaque marker that allows fluoroscopic verification of the position of the catheter. Balloon 20 is preferably elastomeric, having an initial inflated and wrinkle-free diameter, and being elastically expandable upon further filling.

Figure 2C:
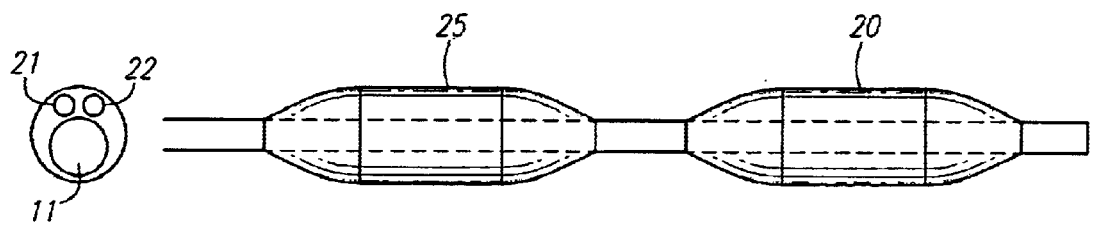
FIG. 2C depicts another embodiment of the devices having two expandable members for providing partial obstruction of a vessel.
Figure 2D:
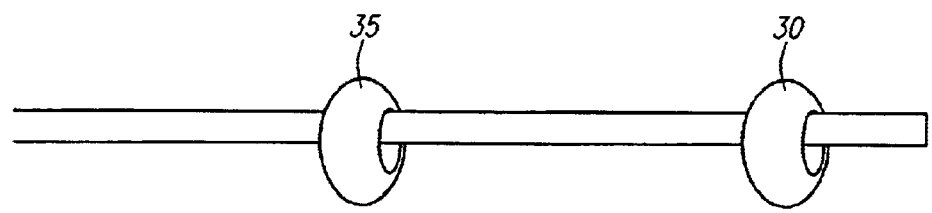
FIG. 2D depicts another embodiment of the devices having two obstruction members.

FIG. 2C depicts another embodiment of the device having first expandable member 20 that communicates with inflation lumen 21, and second expandable member 25 that communicates with inflation lumen 22. FIG. 2D depicts another embodiment of the device having first constrictor 30 and second constrictor 35 that allow passage of blood through the expandable members when deployed.

Figure 3A:
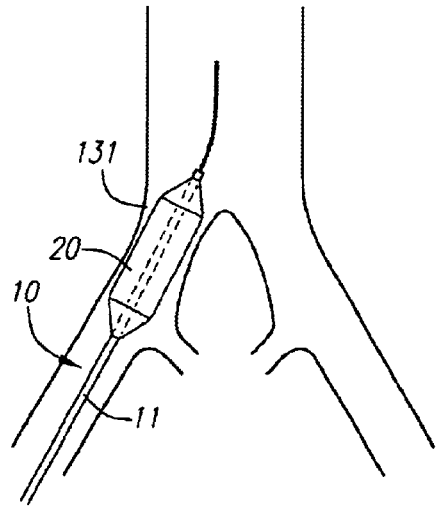
FIG. 3A depicts the device of FIG. 2B inserted in the right common iliac artery.

In use, as depicted in FIG. 3A, catheter 10 of FIG. 2A having balloon 20 in a collapsed state is positioned in one of left common iliac artery 132 or right common iliac artery 131 after insertion through an incision made in a peripheral artery, such as the femoral artery. A baseline cerebral blood flow is measured before, during, or after positioning the catheter. After the position in the artery is verified under fluoroscopy, balloon 20 is expanded to partially or completely occlude the right iliac artery, thereby enhancing cerebral blood flow. The level of occlusion of the right iliac artery is adjusted to achieve a desired increase in cerebral blood flow. By this method, cerebral blood flow may be enhanced in conditions of cerebral ischemia, where autoregulatory mechanisms are impaired. As described in copending application Ser. No. 09/841,929, filed Apr. 24, 2001 (incorporated herein by reference in its entirety), a small increase in pressure, resulting from obstruction of a major blood vessel, results in a disproportionate increase in perfusion of cerebral tissue that has impaired autoregulatory function.

Figure 3B:
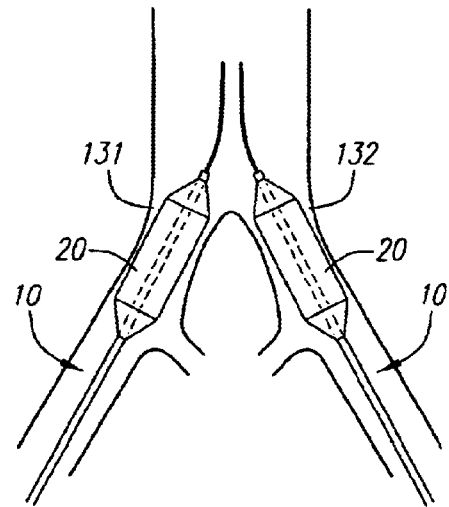
FIG. 3B depicts devices of FIG. 2B inserted in the night and left common iliac arteries.

Alternatively, catheters 10 of FIG. 2B are positioned in right common iliac artery 131 and in left common iliac artery 132 as shown in FIG. 3B. Balloons 20 are expanded to partially or completely occlude the common iliac arteries, thereby enhancing cerebral blood flow.

Figure 4A:
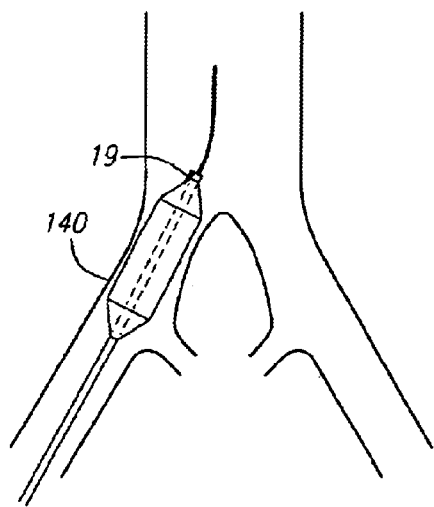
FIG. 4A depicts the device of FIG. 2B inserted in the right femoral artery.
Figure 4B:
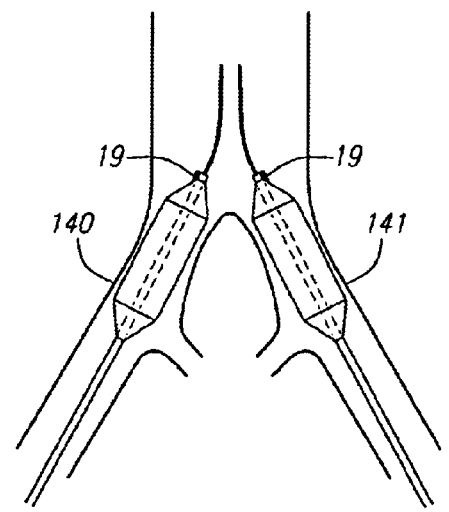
FIG. 4B depicts devices of FIG. 2B inserted in the right and left femoral arteries.

Augmentation of cerebral blood flow may also be achieved by inserting catheter 10 of FIG. 2B in one of left femoral artery 141 or right femoral artery 140 as depicted in FIG. 4A. Alternatively, catheters 10 may be inserted in right femoral artery 140 and left femoral artery 141 as shown in FIG. 4B. In certain embodiments, the distal end of the catheter also includes manometer 19 for measuring blood pressure distal the catheter, i.e., upstream of the expandable member. Pressure measurement may be taken by use of a lumen extending through the catheter and in fluid communication with a pressure transducer.

Figure 5A:
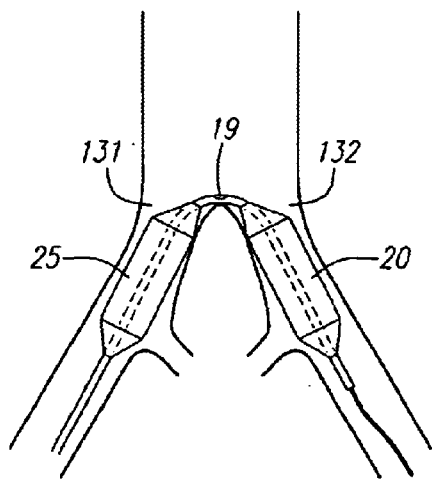
FIG. 5A depicts the device of FIG. 2C inserted in the right and left external iliac arteries.
Figure 5B:
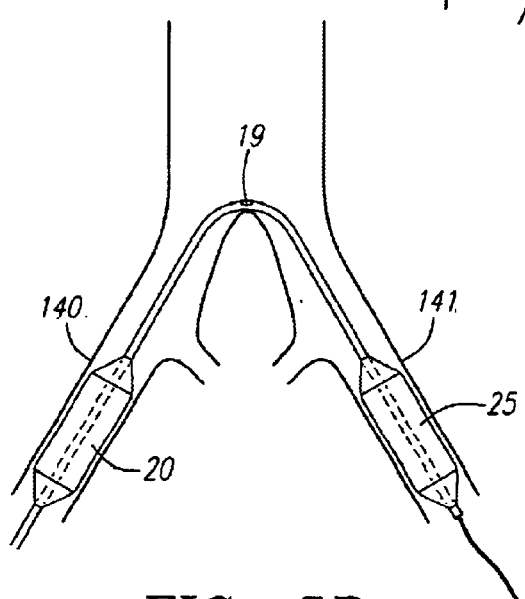
FIG. 5B depicts the device of FIG. 2C inserted in the right and left femoral arteries.

In FIG. 5A, catheter 10 of FIG. 2C having balloons 20 and 25 is inserted through an incision in a peripheral artery, such as the right femoral artery. Balloon 25 is positioned in right common iliac artery 131 and balloon 20 is positioned in left common iliac artery 132. By expanding balloons 20 and 25, arterial blood flow to the lower extremities is partially or completely obstructed, enhancing cerebral blood flow. Manometer 19, such as a lumen that is in fluid communication with the aorta-iliac bifurcation and a pressure transducer, is preferably included in the catheter 10. Pressure can be measured before, during, and/or after the inflation of balloons 20 and 25. Similarly, as shown in FIG. 5B, catheter 10 of FIG. 2C is inserted through the left femoral artery, with balloon 20 positioned in right femoral artery 140 and balloon 25 positioned in left femoral artery 141. Blood pressure in the left femoral artery is measured by manometer 19. Obstruction of the right and left femoral artery is adjusted to achieve a desired increase in cerebral blood flow.

Figure 6:
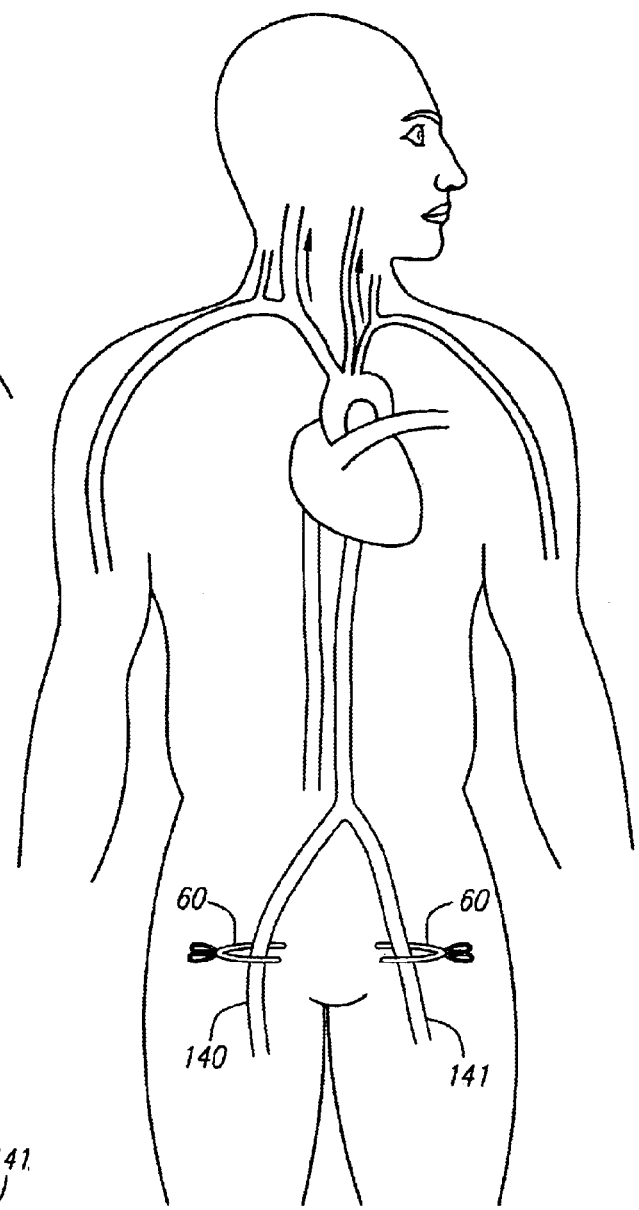
FIG. 6 depicts application of C-clamps over the right and left femoral arteries.

Enhancement of cerebral blood flow may also be achieved by external compression of the femoral arteries as shown in FIG. 6. C-clamp 60 is shown compressing right femoral artery 140 and left femoral artery 141 after incisions are made over the femoral arteries. The right and left common iliac arteries could alternatively be clamped. Desired increase in cerebral blood flow is achieved by adjusting the compression of the arteries by the clamps. Damaging ischemia of the extremities may be avoided by periodically releasing the clamp and allowing perfusion to the distal extremities. Doppler ultrasound may be used to monitor distal blood flow. Obstruction of femoral blood flow may also be achieved by applying tourniquets to the femoral arteries or the legs, which, in turn, compresses the femoral arteries. External compression has the advantage of being completely non-invasive. Further augmentation of cerebral blood flow can be accomplished by external compression of one or both upper arms by clamping or use of tourniquet(s). Similar to the effect on the femoral artery, external limb compression of the upper arms compresses the brachial artery, causing incremental blood pressure increase in the aorta, and more significantly, blood flow increase to the brain.

Figure 7:
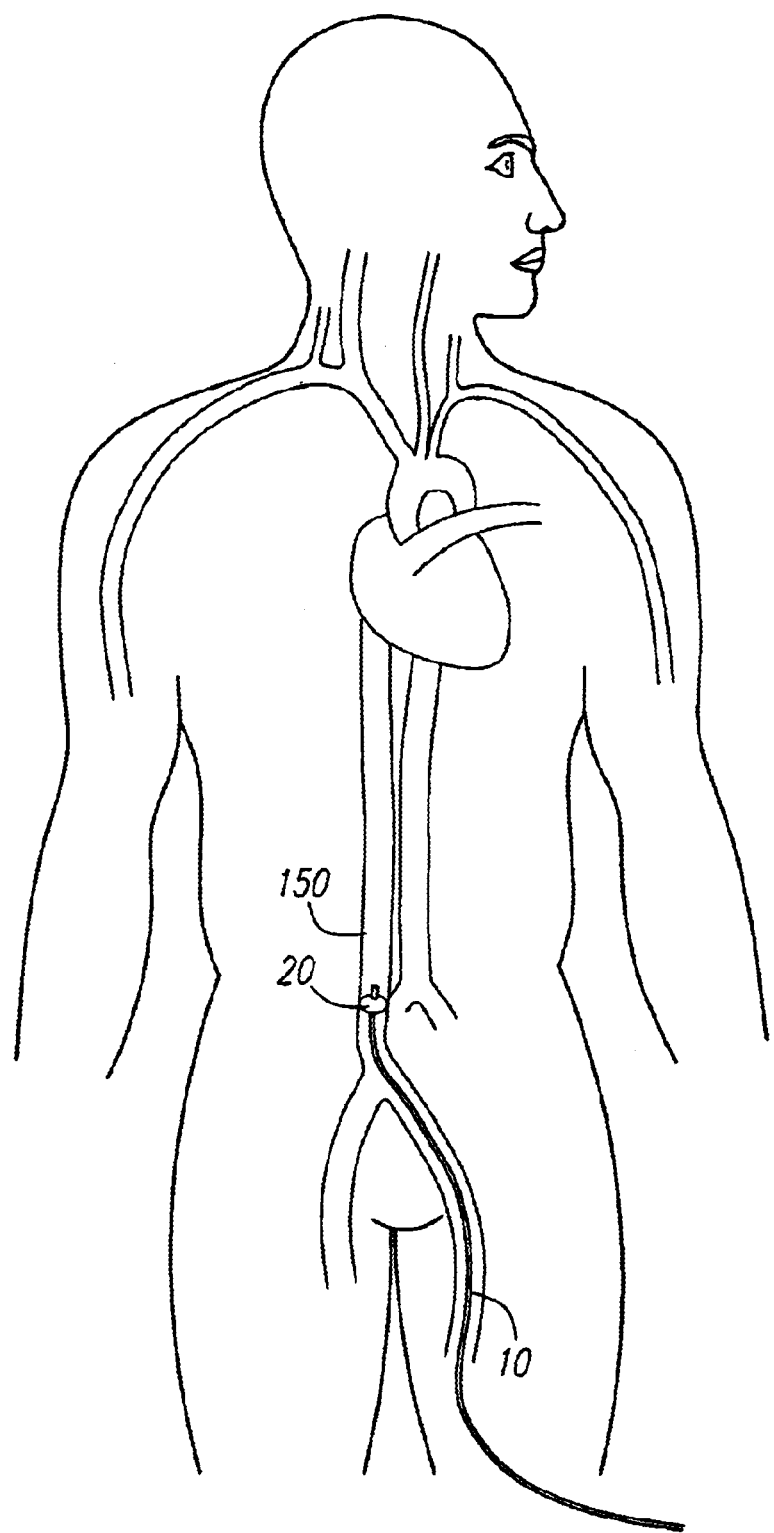
FIG. 7 depicts the device of FIG. 2B inserted in the inferior vena cava through a left femoral incision.

In FIG. 7, catheter 10 of FIG. 2B is inserted through an incision in the left femoral vein into inferior vena cava 150. Balloon 20 is inflated to partially or completely obstruct the vena cava, causing upstream peripheral venous pressure to increase, which in turn elevates mean arterial pressure (by action through the capillary bed) and induces increased cerebral blood flow. The desired increase in cerebral blood flow is achieved by adjusting the obstruction in the vena cava.

Figure 8:
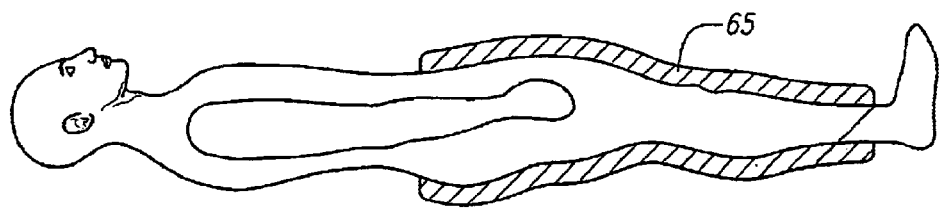
FIG. 8 depicts application of compression pants to the lower extremities of a patient.

Obstruction of the peripheral vasculature to induce an increase in cerebral blood flow may also be achieved by applying external compression, through the use of compression pants 65, to a patient's lower extremities as shown in FIG. 8. Compression pants are known in the art, and are used in a pulsatile fashion called "external counterpulsation" synchronous with the heart beat, in order to augment cardiac output. While external counterpulsation has been used in a synchronized pulsatile fashion, when used in a static mode a substantial impact on cerebral blood flow can be achieved. External counterpulsation can also be used in a semi-static mode, allowing for periodic limb reperfusion. Compression of the extremities is adjusted to achieve the desired increase in cerebral blood flow. Static compression of one or two legs has the advantage of not only increasing afterload (by peripheral arterial and venous obstruction), but it also squeezes the venous blood to the rest of the body, mimicking volume loading. These effects combine to yield desired hemodynamic effects needed to increase cerebral blood flow. It is also contemplated that synchronous external counterpulsation, with timing optimized, may significantly increase cerebral blood flow, and be useful for treating cerebral ischemia.

Figure 9:
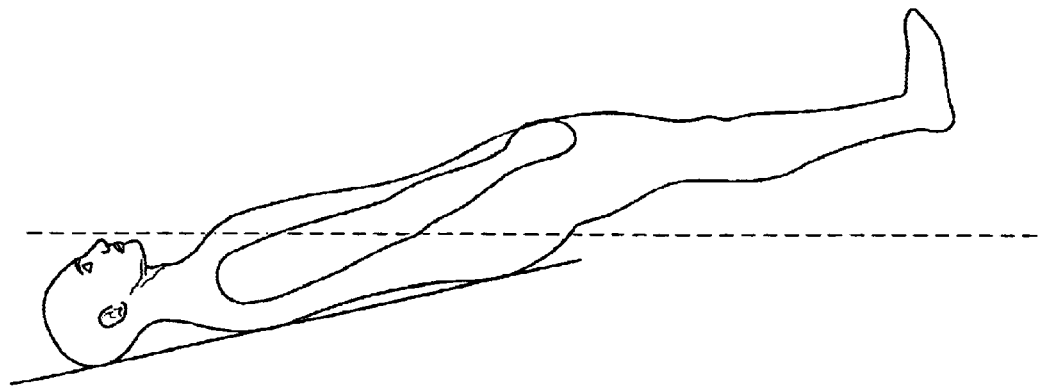
FIG. 9 depicts a patient placed in a trendelenberg position to enhance cerebral blood flow.

Increase in cerebral flow may also be achieved by placing a patient in a trendelenberg position, wherein the patient's head is positioned below the horizontal as shown in FIG. 9. The angle of the patient relative to the horizontal is adjusted to be approximately 5°, 10°, 15°, or other appropriate number of degrees below horizontal to achieve a desired increase in cerebral blood flow, as measured, for example, by transcranial doppler (TCD).

Figure 10:
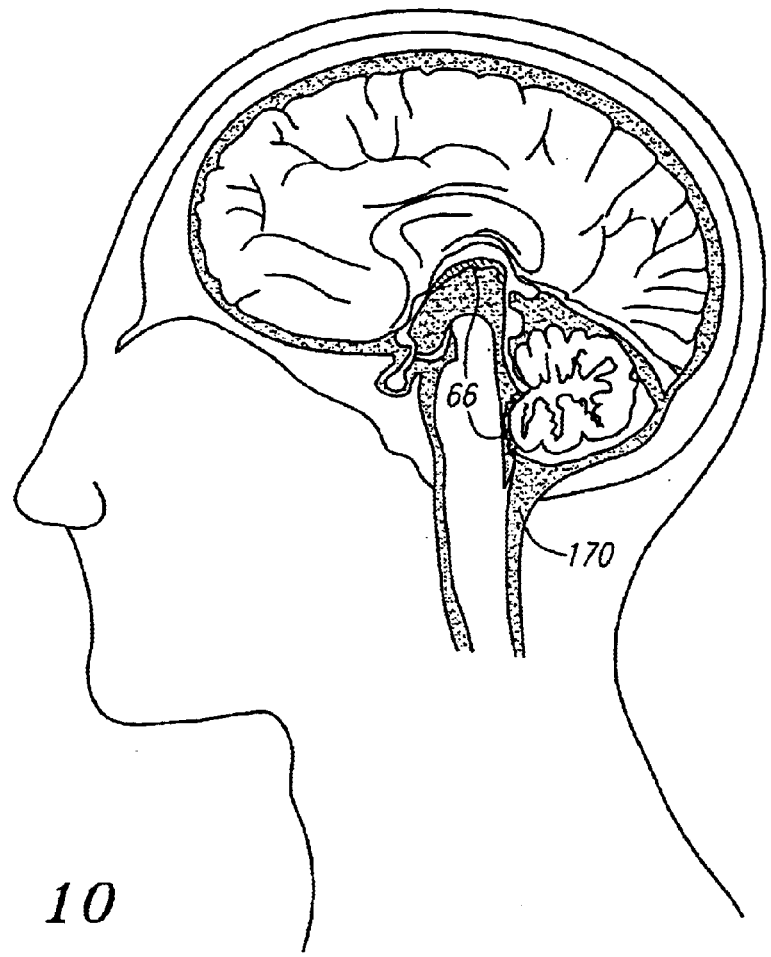
FIG. 10 depicts a cross sectional view of a patient's brain showing the subarachnoid spaces and cisterns.
Figure 10A:
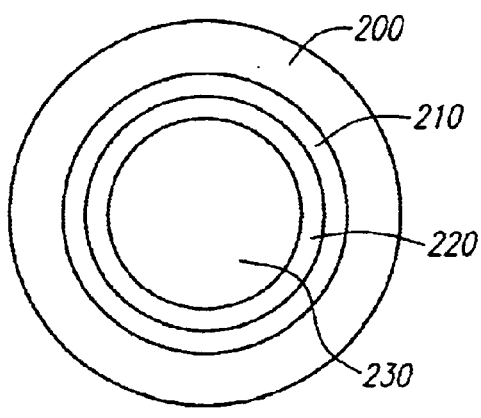
FIG. 10A depicts a diagram illustrating volumes of braincase tissues and fluids.
Figure 10B:
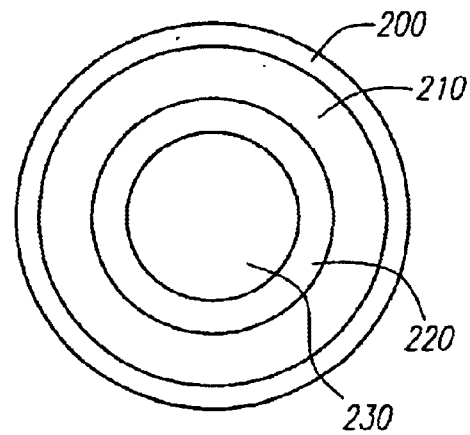
FIG. 10B depicts the change in the volumes of braincase tissues and fluids after removal of a portion of cerebral spinal fluid.

Cerebral blood flow may also be increased by manipulating the volume of the cerebral spinal fluid (CSF). The CSF that is produced by choroids plexus 66 within the ventricles of the brain circulates around and cushions the brain as depicted in FIG. 10. Since the volume of the braincase is fixed, all the tissues and fluid within the braincase must remain constant. This volume may be expressed as:

Braincase volume=volume of $CSF$+brain tissue volume+arterial volume+venous volume Assuming that the brain tissue volume is constant, a decrease in the volume of the CSF will produce an increase in the arterial and venous volume. This concept is illustrated in FIGS. 10A and 10B. FIG. 10A shows the composition of a normal braincase volume having brain tissue volume 230, venous volume 220, arterial volume 210, and CSF volume 200. When a portion of CSF is removed, CSF volume 200 decreases and is compensated by an increase in arterial volume 210 and venous volume 220 as shown in FIG. 10B. This leads to an increase in arterial flow rate, and cerebral blood flow. A volume of 10 cc, 15 cc, 20 cc, 25 cc, 30 cc or more of CSF may be removed from the epidural space through a lumbar puncture, a burr hole, or a cerebellomedullary cistern 170 puncture. Alternatively, a catheter may be inserted in the epidural space for continuous withdrawal of CSF at a slow rate to maintain CSF volume at a reduced level to increase cerebral blood flow.

Figure 11:
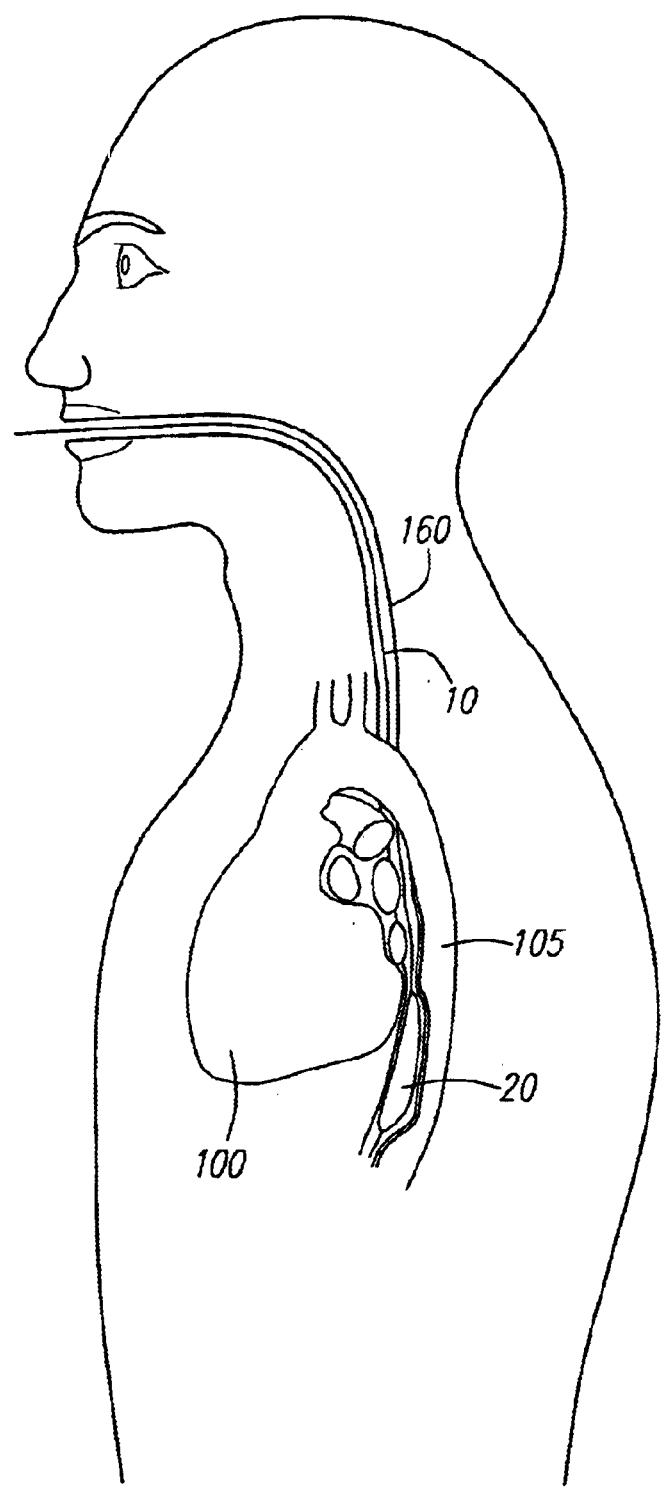
FIG. 11 depicts trans-esophageal compression of the descending aorta to enhance cerebral blood flow.

Increase in cerebral flow may also be achieved by compression of the descending aorta as shown in FIG. 11. Catheter 10 is inserted through esophagus 160 until balloon 20 reaches a segment of the esophagus that is immediately adjacent descending aorta 105. Balloon 20 is inflated, dilating esophagus 160, and compressing descending aorta 105. Balloon inflation is adjusted to achieve a desired increase in cerebral blood flow, as measured, for example, by transcranial doppler (TCD).

It will further be understood that, when the above methods and devices are applied, there may be a sharp increase in cerebral blood flow. The initial percent increase in cerebral blood flow rate may decay with time after the initial application of the above methods and devices. This decay is possibly due to autoregulation within the brain. When the constriction or other treatment is released, even for a short time (e.g., 10 seconds, 20 seconds, 30 seconds, 1 minute, or more), and then applied again, there is again a sharp increase in cerebral blood flow followed by gradual decay. Thus, one contemplated treatment regimen would include periodic (every 30 minutes or one hour) release of constriction or other treatment disclosed herein to "reset" the autoregulatory system followed by re-application of treatment. Another contemplated treatment regimen would include a gradual increase in constriction or other treatment with time in order to maintain an approximately constant rate of increased cerebral blood flow.

Although the foregoing invention has, for the purposes of clarity and understanding, been described in some detail by way of illustration and example, it will be understood that certain changes and modifications may be practiced which will still fall within the scope of the appended claims. In particular, it should be understood that any feature shown in any figure or embodiment can be used as a component or feature of any device in any other figure or embodiment.

What is claimed is:

1. A method for enhancing cerebral blood flow in a patient, comprising the steps of:

measuring a baseline cerebral blood flow;

inserting a first expandable member into at least one of a right femoral artery and/or a right iliac artery and expanding the first expandable member to at least partially obstruct the at least one right femoral artery and/or right iliac artery;

inserting a second expandable member into at least one of a left femoral artery and/or a left iliac artery and expanding the second expandable member to at least partially obstruct the at least one left femoral artery and/or left iliac artery;

measuring an enhanced cerebral blood flow after the at least partial obstruction of the right and left femoral artery and/or iliac artery; and comparing the enhanced cerebral blood flow to the baseline cerebral blood flow.

2. The method of claim 1, further comprising the step of adjusting the level of obstruction of the right femoral artery and/or the left femoral artery to achieve a desired increase in cerebral blood flow.

3. The method of claim 2, wherein the desired increase in cerebral blood flow is 25 percent or more.

4. The method of claim 1, further comprising the step of adjusting the level of obstruction of the right iliac artery and/or the left iliac artery to achieve a desired increase in cerebral blood flow.

5. The method of claim 1, wherein the first and second expandable members are balloons.

6. The method of claim 1, wherein at least one of the first and second expandable members is expanded to fully obstruct a least one of the right femoral artery and/or the right iliac artery.

7. The method of claim 1, further comprising the step of measuring blood pressure in the femoral or iliac arteries using a manometer mounted distal to the expandable members.

8. The method of claim 1, wherein the expandable members communicate with inflation lumens.

* * * * *